US00PP26302P3

(12) United States Plant Patent
Brown

(10) Patent No.: US PP26,302 P3
(45) Date of Patent: Jan. 12, 2016

(54) ***MANDEVILLA* PLANT NAMED 'KLEMS14012'**

(50) Latin Name: *Mandevilla sanderi*
Varietal Denomination: KLEMS14012

(71) Applicant: Klemm+Sohn GmbH & Co. KG, Stuttgart (DE)

(72) Inventor: Graham Noel Brown, Pennant Hills (AU)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 113 days.

(21) Appl. No.: 14/120,201

(22) Filed: May 5, 2014

(65) Prior Publication Data

US 2015/0319898 P1 Nov. 5, 2015

(51) Int. Cl.
*A01H 5/00* (2006.01)

(52) U.S. Cl.
USPC ..... Plt./232

(58) Field of Classification Search
USPC ..... Plt./232
See application file for complete search history.

*Primary Examiner* — Annette Para
(74) *Attorney, Agent, or Firm* — Barbara Campbell; Bethany R. Roahrig; Cochran Freund & Young, LLC

(57) ABSTRACT

A new *mandevilla* plant particularly distinguished by red flowers, earliness to flower, a good branching habit, a compact plant habit, and a trailing growth habit, is disclosed.

1 Drawing Sheet

Genus and species: *Mandevilla sanderi.*
Variety denomination: 'KLEMS14012'.

BACKGROUND OF THE NEW PLANT

The present invention comprises a new and distinct variety of *mandevilla*, botanically known as *Mandevilla sanderi* and hereinafter referred to by the variety name 'KLEMS14012'. 'KLEMS14012' was derived as a selection from a hand-pollination conducted in Cobbity, New South Wales, Australia in January 2011 between the proprietary female parent '11.5.1' (unpatented) and the proprietary male parent '11.5.7'.

In October 2011, a single plant was selected in Cobbity, New South Wales, Australia from plants produced from the initial hand-pollination. In November 2011, 'KLEMS14012' was first asexually propagated by vegetative cuttings. 'KLEMS14012' was found to reproduce true to type in successive generations of asexual propagation via vegetative cuttings in Cobbity, New South Wales, Australia, Stuttgart, Germany, and Nairobi, Kenya.

SUMMARY

The following are the most outstanding and distinguishing characteristics of this new variety when grown under normal horticultural practices in Cobbity, New South Wales, Australia, Stuttgart, Germany, and Nairobi, Kenya.

1. Red flowers;
2. Earliness to flower;
3. A good branching habit; and
4. A compact plant habit and a trailing growth habit.

DESCRIPTION OF THE PHOTOGRAPH

This new *mandevilla* plant is illustrated by the accompanying photograph which shows the flowers, the foliage, and an overall view of the plant. The photograph is of a plant approximately five-months-old grown outdoors in Stuttgart, Germany in July 2013. The colors shown are as true as can be reasonably obtained by conventional photographic procedures.

DESCRIPTION OF THE NEW VARIETY

The following detailed descriptions set forth the distinctive characteristics of 'KLEMS14012'. The data which define these characteristics were collected from asexual reproductions carried out in Stuttgart, Germany. Data was collected on six-month-old plants grown indoors in Stuttgart, Germany under greenhouse and outdoor conditions in late summer 2013. Color references are to The R.H.S. Colour Chart of The Royal Horticultural Society of London (R.H.S.), 5$^{th}$ edition (2007).

Classification:
- *Family.*—Apocynaceae.
- *Species.*—*Mandevilla sanderi.*
- *Common name.*—*Mandevilla.*
- *Variety.*—'KLEMS14012'.

Parentage:
- *Female.*—Proprietary *mandevilla* parent '11.5.1' (unpatented).
- *Male.*—Proprietary *mandevilla* parent '11.5.7' (unpatented).

Propagation:
- *Type.*—Cuttings.
- *Time to produce a rooted young plant.*—8 weeks.
- *Root description.*—Does not develop bulbs, corms, or rhizomes; root structure is ovate.
- *Rooting habit.*—Normal.

Plant:
- *Plant and growth habit.*—Compact plant habit but a trailing growth habit.
- *Plant height.*—40.0 cm.
- *Plant diameter.*—30.0 cm.

Lateral branches:
- *Branching habit.*—Moderate.
- *Length*—Approximately 50.0 cm.
- *Diameter.*—0.3 cm.
- *Internode length.*—Between 1.0 cm and 30.0 cm.
- *Strength.*—Medium.
- *Texture.*—Glossy, shiny, and no pubescence.
- *Color.*—RHS 141D.

Foliage:
*Arrangement*.—Opposite.
*Length*.—About 4.0 cm.
*Width*.—About 2.0 cm.
*Shape*.—Composed.
*Apex*.—Cuspidate.
*Base*.—Obtuse.
*Margin*.—Entire.
*Texture*.—Upper surface: Glossy, shiny, no pubescence. Lower surface: Leathery and dull.
*Venation pattern*.—Pinnate.
*Color, developing leaves*.—Upper surface: RHS 141A. Lower surface: RHS 141C.
*Color, expanded leaves*.—Upper surface: RHS 141A. Lower surface: RHS 141C.
Petioles:
*Length*.—About 2.0 cm.
*Diameter*.—About 0.1 cm.
*Texture and appearance* (*both upper and lower surfaces*).—Smooth and dull.
*Color*.—Upper surface: RHS 141B. Lower surface: RHS 141D.
Flower bud:
*Height*.—About 4.0 cm.
*Diameter*.—About 1.0 cm.
*Shape*.—Tall, cylinder.
*Color*.—RHS 45C.
Flower:
*Flower type and habit*.—Single.
*Natural flowering season*.—Spring and summer.
*Flower longevity on the plant*.—About 14 days.
*Fragrance*.—Absent.
*Appearance*.—Glossy and satiny.
*Diameter*.—5.0 cm.
*Length*.—4.0 cm.
Corolla:
*Arrangement and appearance*.—Radial.
*Petal lobe length*.—2.0 cm.
*Petal lobe width*.—2.0 cm.
*Petal lobe shape*.—Round.
*Petal lobe apex*.—Obtuse.
*Petal lobe margin*.—Entire.
*Petal lobe texture* (*both upper and lower surfaces*).—Glossy and shiny; pubescence is sparse.
*Petal lobe color, when opening and fully opened*.—Upper surface: RHS 45A. Lower surface: RHS 45B.
*Throat diameter*.—2.5 cm.
*Throat texture*.—Very short hairs, satiny.
*Throat color*.—RHS 29A.
*Tube length*.—3.0 cm.
*Tube diameter*.—0.5 cm at the base.
*Tube color*.—RHS 45D.
*Tube texture*.—Satiny.
Sepals:
*Arrangement and appearance*.—Fused and dull.
*Length*.—2.0 cm.
*Width*.—0.3 cm.
*Shape*.—Lanceolate.
*Apex*.—Obtuse.
*Margin*.—Entire.
*Texture*.—Pubescence is present (sparse).
*Appearance* (*both upper and lower surfaces*).—Dull.
*Color*.—Inner surface: RHS 140B. Outer surface: RHS 140C.
Peduncles:
*Length*.—2.0 cm.
*Diameter*.—0.1 cm.
*Appearance*.—Dull.
*Texture*.—Pubescence is present (sparse).
*Strength*.—Moderate.
*Color*.—RHS 140C.
Pedicels:
*Length*.—4.0 cm.
*Diameter*.—0.1 cm.
*Appearance*.—Dull.
*Texture*.—Pubescence is present (sparse).
*Strength*.—Strong.
*Aspect*.—Erect.
*Color*.—RHS 140C.
Reproductive organs:
*Stamens*.—Quantity per flower: Greater than 1. Filament length: Less than 0.5 cm. Filament color: RHS 24B. Anther size: 0.1 cm. Anther color: RHS 24B. Pollen amount: Absent.
*Pistils*.—Quantity per flower: 1. Pistil length: 0.4 cm. Stigma shape: Ovate. Stigma color: RHS 24A. Style length: 0.1 cm. Style color: RHS 24B. Ovary color: RHS 24B.
Fruit and seed set: None observed.
Disease and pest resistance: None observed.

COMPARISON WITH PARENTAL LINE AND KNOWN VARIETY

'KLEMS14012' is a distinct variety of *mandevilla* having red flowers. 'KLEMS14012' is distinguished from its parents as described in Table 1.

TABLE 1

| Characteristic | Variety 'KLEMS14012' | Female Parent '11.5.1' | Male Parent '11.5.7' |
|---|---|---|---|
| Cold tolerance | Very good | Less than 'KLEMS14012' | Good |
| Earliness to flower | Early | Early | Late |
| Growth habit | Compact | Medium | Medium |

'KLEMS14012' can be compared to the commercial *mandevilla* plant variety 'Tropidenia' (patent status unknown). Differences between the two varieties are described in Table 2.

TABLE 2

| Characteristic | Variety 'KLEMS14012' | Commercial line 'Tropidenia' |
|---|---|---|
| Flower richness | Very good | Medium |
| Branching | Good | Less than 'KLEMS14012' |

I claim:

1. A new and distinct variety of *mandevilla* plant named 'KLEMS14012' as shown and described herein.

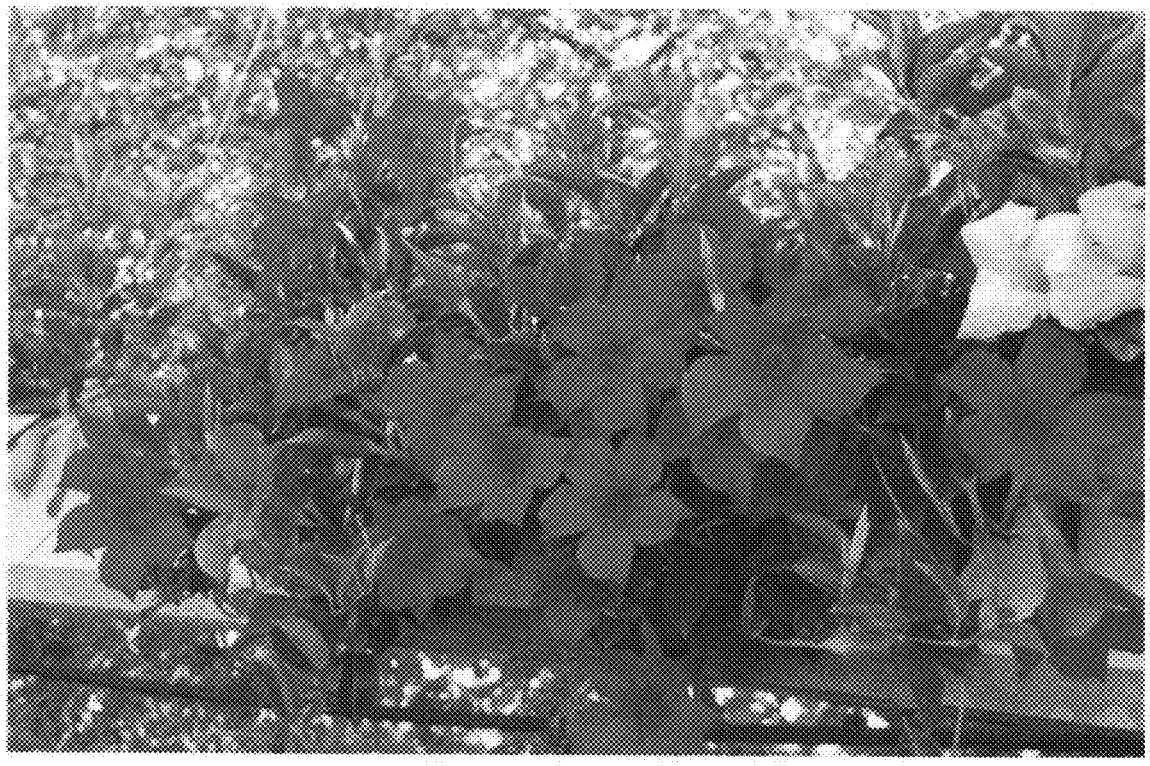

* * * * *